United States Patent [19]

Dannenberg et al.

[11] 4,285,884
[45] Aug. 25, 1981

[54] PROCESS FOR RESOLUTION OF RACEMIC DL-α-AMINOCARBOXYLIC ACIDS

[75] Inventors: Wolfgang Dannenberg, Wunstorf; Horst Schmand, Bad Nenndorf, both of Fed. Rep. of Germany

[73] Assignee: Riedel-de Haen Aktiengesellschaft, Seelze, Fed. Rep. of Germany

[21] Appl. No.: 956,450

[22] Filed: Nov. 1, 1978

[30] Foreign Application Priority Data

Nov. 3, 1977 [DE] Fed. Rep. of Germany ....... 2749203

[51] Int. Cl.$^3$ ................. C07C 101/04; C07C 101/06; C07C 101/08; C07B 19/00
[52] U.S. Cl. .............................. 260/501.11; 562/401
[58] Field of Search ............... 562/401, 444, 445, 553; 260/501.11

[56] References Cited

U.S. PATENT DOCUMENTS

| 3,976,680 | 8/1976 | Clark et al. ........................ 562/401 |
| 4,048,224 | 9/1977 | Chemerda et al. ................. 562/401 |

FOREIGN PATENT DOCUMENTS

| 2025819 | 12/1970 | Fed. Rep. of Germany . |
| 2147620 | 3/1972 | Fed. Rep. of Germany . |
| 2147629 | 3/1972 | Fed. Rep. of Germany . |
| 2309180 | 8/1973 | Fed. Rep. of Germany . |
| 2355785 | 5/1974 | Fed. Rep. of Germany . |
| 2400489 | 7/1974 | Fed. Rep. of Germany . |
| 2322412 | 11/1974 | Fed. Rep. of Germany . |
| 2449492 | 4/1975 | Fed. Rep. of Germany . |
| 1240687 | 7/1971 | United Kingdom . |
| 1241844 | 8/1971 | United Kingdom . |
| 1382687 | 2/1975 | United Kingdom . |

OTHER PUBLICATIONS

Bergmann et al., *Zeitschrift fuer Physiol., Chemie*, vol. 152, pp. 282–299, (1926).
Sheehan et al., *Journal of Organic Chemistry*, vol. 84, pp. 2417–2420, (1962).
Halpern et al., *Chemistry and Industry*, pp. 1399–1400, Aug. 17, 1963.
Hiskey et al., Journal of Organic Chemistry, vol. 31, pp. 3582–3587 (1966).
Kaneko et al., *Synthetic Production and Utilization of Amino Acids*, pp. 26 and 28, (1974).
Williams, Chemical Abstracts, vol. 80, article 105971t, (1974).
Bergmann et al., *Chem. Ber.*, 58, 1034, (1925).
McIntire, *J. Amer. Chem. Soc.*, 69, 1377, (1947).
Turner, *Quart. Rev.*, 1, p. 299 et seq. (1947).
Weiland et al. Ann. Chem. 576, 104, (1952).
*Biochem. J.* 121, p. 425, (1971).
Wilen, "Tables of Resolving Agents and Optical Resolution" Notre Danem Ubduabam (1972).
*Chem. Abs.* vol. 81, 105971t (1974).

*Primary Examiner*—Natalie Trousof
*Assistant Examiner*—Vera C. Clarke
*Attorney, Agent, or Firm*—Curtis, Morris & Safford

[57] ABSTRACT

In a process for resolving racemic DL-α-aminocarboxylic acids the said acids are reacted in an inert solvent with an aromatic o-hydroxy aldehyde to obtain an azomethine derivative which is reacted in the same stage with an optically active amine base to give a salt. The diastereomeric salt obtained is separated and the respective optically active α-aminocarboxylic acid is obtained therefrom by an acid treatment. By this process aliphatic and aromatic α-amino-carboxylic acids can be resolved, especially p-hydroxyphenyl glycine.

23 Claims, No Drawings

PROCESS FOR RESOLUTION OF RACEMIC DL-α-AMINOCARBOXYLIC ACIDS

This invention relates to a process for resolution of racemic DL-α-aminocarboxylic acids of the formula II

in which R is lower alkyl, optionally substituted phenyl or benzyl, by salt formation with an optically active amine base. More particularly, the invention relates to a process for chemical resolution of racemic types of α-amino-4-hydroxyphenylacetic acid.

α-amine-4-hydroxyphenylacetic acid and the derivatives thereof are important intermediates for the manufacture of synthetic penicillins and cephalosporins. Of the two possible enantiomers the D(−)-isomer is preferred because of its higher pharmaceutical efficacy in synthetic penicillin and cephalosporin compounds. Therefore, the manufacture of DL-α-amino-4-hydroxyphenylacetic acid and its resolution into optical antipodes has found much interest.

Processes for the manufacture of DL-α-amino-4-hydroxyphenylacetic acid and its derivatives and for resolving the same into the optical antipodes have been proposed.

In British Specification No. 1,240,687, for example, DL-chloro-acetylamino-4-methoxyphenylacetic acid is treated with swine kidney acylase whereby the L-form is selectively deacetylized. The D-acyl form separated by extraction is then hydrolized in boiling hydrochloric acid and demethylated with hydrobromic acid. In DE-OS No. 2,322,412 and DE-OS No. 2,449,492 a chemical splitting into the optical antipodes is brought about by salt formation of N,O-diacetyl and N-benzoyl-amino-acid with the aid of (+)-α-phenylethylamine. After liberation of the amine base, the crystallized compounds are hydrolyzed in boiling hydrochloric acid.

British Specification No. 1,241,844 and DE-OS No. 2,025,819 describe a chemical resolution with quinine trihydrate. Prior to this reaction the amino group must be protected by a carbobenzoxy function. After liberation of the optically active base, the crystalline fraction can be transformed into the free amino-acid by catalytical hydrogenation.

In DE-OS No. 2,147,620 there is proposed a process for the resolution of the racemic N,O-diacyl derivative of DL-α-amino-4-hydroxyphenylacetic acid with the use of dehydroabietyl amine.

DE-OS No. 2,355,785 also describes a racemic resolution of the N,O-diacyl compound with cinchonidine. The free amino acid can be obtained after a treatment with boiling hydrochloric acid.

Biochem. J., 121, page 425 (1971) reports the resolution with bromocamphorsulfonic acid.

All methods previously proposed have, however, a series of disadvantages: Enzymatic processes are very expensive and complicated due to the difficult isolation and purification of the required enzymes and to their instability.

In most cases chemical processes for the resolution of racemates by formation of diastereomeric salts of N-substituted amino-acids and optically active amine bases give very low total yields of D(−)-amino acid. In many cases the components must be dissolved in large amounts of solvent and very often the diastereomeric salts formed must be purified by recrystallization to ensure a sufficient optical purity of the resulting amino-acid. Besides the high price for the optically active amine bases, a further drawback resides in the necessary introduction and splitting off of the N-protective groups, which procedures involve losses in yield. Finally, bromocamphorsulfonic acid, which can be used as such without formation of derivatives, has the drawback of being very expensive.

Therefore, a process for chemical resolution of racemic forms of α-amino-4-hydroxyphenylacetic acid has been developed which does not have the aforesaid disadvantages and the principle of which can be used quite generally for splitting other racemic α-aminocarboxylic acids of formula II.

It is the object of the present invention to provide a process for splitting racemic α-aminocarboxylic acids which comprises (a) reacting a DL-α-aminocarboxylic acid of the formula II as defined above, in an inert solvent or solvent mixture, with an aromatic aldehyde of the formula III

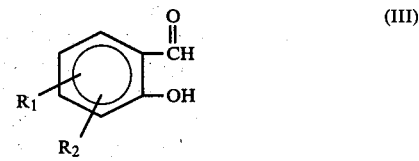

in which R1 and R2, which can be identical or different, are hydrogen, halogen, lower alkyl or lower alkoxy, and two adjacent alkyl substituents are possibly fused to form a second benzene nucleus, to give an azomethine derivative and reacting the azomethine derivative in the same reaction stage with the optically active amine base to give a salt;

(b) separating by crystallization the diastereomeric salt of the amine base and the azomethine derivative of the α-aminocarboxylic acid and the aromatic aldehyde and (c) liberating the optically active α-aminocarboxylic acid by treating the separated salt with a strong acid.

To liberate the optically active amino-acid the separated salts are simply acidified with a strong acid without racemization taking place.

Azomethines of aromatic aldehydes and amino-acids became known early by the publications of the Bergmann school (M. Bergmann, H. Ennslin, L. Zervas, Chem.Ber. 58, 1034 (1925)). They have been isolated exclusively in the form of their alkaline earth metal salts or alkaloid salts. Wieland et al. (T. Wieland, W. Schäfer, Ann.CHem. 576, 104 (1952)), prepared the potassium salt of N-benzyliden-glycine and transformed it by the mixed anhydride method into the thiophenyl ester.

McIntire was the first to show that 5-chlorosalicyl aldehyde and 2-hydroxynaphthyl aldehyde-(1) form stable and well crystallizing azomethines with free amino-acids (F. C. McIntire, J.Amer.Chem.Soc., 69, 1377 (1947)).

The novel amine salts according to the invention differ from the aforesaid compounds in that they are diastereomeric salts obtained from racemic mixtures of α-amino-acids which can be separated into their stereo-isomers. Alkali metal salts prepared from racemic mixtures of α-amino-acids are not diastereomeric salts and they cannot be separated into their stereoisomers without use of chiralic auxiliaries. Separation into the diastereomers of the alkaloid salts isolated by Bergmann et al. (Chem.Ber. 58, 1034 (1925)) has not yet been described.

The process for separating racemates described in DE-OS No. 2,400,489 via separating diastereomeric salts of optically active amine bases and enamine derivatives of α-aminocarboxylic acids has several disadvantages as compared with the process of this invention:

The yields obtained in the step of salt formation are in the range of from 60 to 80%, calculated on one enantiomer of the α-amino-acid, in individual cases a yield of 83% is reached. To obtain satisfactory salt yields higher temperatures, in most cases reflux temperature, of the solvent are required for the separation of the water formed. The undesired enantiomer of the amino-acid must be racemized in an additional operation step by usual methods, possibly via the free amino-acid.

With the process of the invention is characterized in that it is not necessary to prepare a derivative from the amino-acid to be split into its optical antipodes. When the reaction components, i.e., amino-acids, optically active amine and aromatic aldehyde, are mixed in a suitable solvent thorough mixing at room temperature brings about salt formation without separation of the water formed. In individual cases, the difference in the solubility of the pair of diastereomeric salts can be so great that yields exceeding 95%, calculated on one enanthiomer of the α-amino-acid, can be obtained.

The racemization on the center of chirality of the amino-acid of the dissolved diastereomeric salt as observed in the process of the invention at room temperature can be utilized in various ways:

By asymmetric transformation of the second order (E. E. Turner, Quart.Rev., 1, pages 299 et seq. (1947),) the yield of the desired diastereomeric salt can be increased in a discontinuous process to an extent such that practically 75% of the racemic amine-acid used is transformed into the D(−)-form. On the other hand, the proportion of amino-acid remaining in solution can be completely racemized at a temperature of from 20° to at most 60° C. without additional operations and recovered in the form of the DL-compound. Other usual operations for racemization of the desired enantiomer can be dispensed with.

It is surprising that such complete racemate separations with utilization of the different solubilities of the diastereomeric salt pair is possible not only with the enamine salts but also with azomethine salts of the amino-acids, and especially with the p-hydroxy-phenyl glycine. The complete reaction of all components without simultaneous precipitation of a diastereomeric salt pair at room temperature and without separation of the water of reaction could not be expected. The readiness of racemization at the center of chirality of the azomethine derivative of the amino-acid in solution is especially surprising since with comparable racemizations of amino-acid derivatives an activation of the center of chirality by addition of ester and nitrile groups has been necessary (Brit. Pat. No. 1,382,687 and DE-OS 2,309,180 relating to asymmetrical transformations of α-amino-nitriles and α-amino-acid esters).

The preparation of the salts of the invention is illustrated by the following scheme:

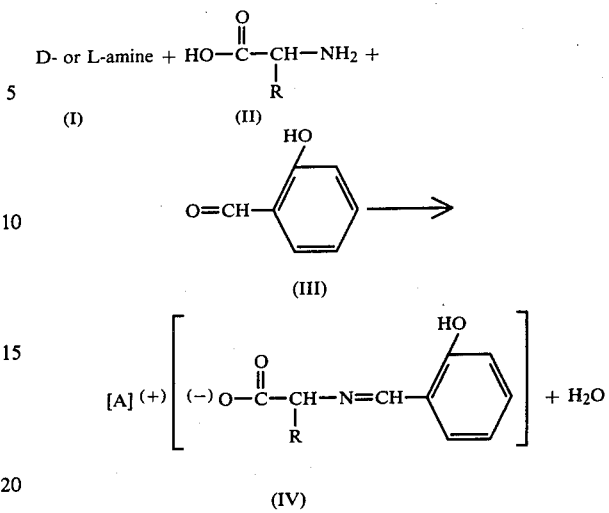

in which A is a cation formed by the addition of a proton on the nitrogen atom of a tertiary, optically active amine base and R is a p-hydroxyphenyl radical, a benzyl radical or an isopropyl radical.

Components I, II, and III are used in the reaction in stoichiometric proportions, i.e., in general in equimolar amounts. The aromatic aldehyde III and the D- or L-amine base I are preferably used in a 10 to 20% excess over the amount of the α-amino-acid II.

To obtain satisfactory results the reaction can be carried out in a wide temperature range, i.e. from about 0° C. to the boiling temperature of the solvent used. It is preferred to carry out the reaction at room temperature while stirring.

In one embodiment of the invention the reaction components are thoroughly mixed by stirring for a period from one to one-hundred sixty hours until the starting compounds are completely dissolved and the salt formed has completely precipitated.

In principle, the water formed in the reaction has no detrimental effect, but it may be removed from the reaction mixture by usual methods.

Suitable inert solvents to be used in the process of the invention are, for example, organic solvents, which do not interfere with the reaction and have no influence whatsoever on the desired direction of the reaction.

Preferred solvents are those which make possible the separation of the diastereomeric salts IV by fractional crystallization, for example, lower alcohols, ethyl acetate, acetonitrile, dimethyl formamide or mixtures thereof. Diethyl ether and similar non polar solvents can be used to dilute the aforesaid solvents.

The amount of solvent to be used in each case can be easily determined by experiments. The most favorable yields are obtained if the reactants pass into solution slowly while the reaction product starts to precipitate.

Depending on the temperature and concentration of the reactants, the aforesaid reaction is complete within a period of about 1 hour to about 48 hours. The progress of the reaction can be readily controlled with the aid of conventional analytical methods.

When the reaction is complete, a mixture of diastereomeric salts of formula IV is obtained as reaction product.

The mixture of diastereomers can be separated by the usual processes, preferably by fractional crystallization.

It is generally known to the expert that it cannot be predicted with certainty which is the most favorable solvent system for a satisfactory separation by fractional crystallization (E. L. Eliel, Stereochemie der Kohlenstoffverbindungen, Weinheim 1966, pages 60 et sq.) and, therefore, for each individual case experiments should be carried out with widely differing solvent systems. Other techniques for the separation of diastereomeric mixtures are known in the art (cf., for example, J. P. Greenstein, M. Winitz, "Chemistry of Amino Acids", New York 1961, chapter 9).

The compounds used as optically active amine bases should have a dissociation constant in the range of from about $10^{-9}$ to $10^{-12}$. Especially suitable are D- and L-isomers of tertiary amines such as N-methyl ephedrine and 1-phenyl-2-dimethylaminopropane-1,3-diol. Salt formation takes also place with numerous other, optically active, tertiary amines. A survey of the most frequently used optically active amines is given by S. H. Wilen in "Tables of Resolving Agents and Optical Resolution", Notre Dame, Indiana (1972).

The aromatic aldehydes used for the formation of the azomethine derivatives should be substituted with a hydroxyl group in ortho-position for stabilization of the azomethine structure (cf. F. C. McIntire, J.Amer.Chem.Soc., 69, 1377 (1947)). Salicyl aldehyde proved to be especially suitable.

The following examples illustrate the invention without limiting same.

It can be seen that by the process of the invention, besides p-hydroxyphenyl glycine quite generally, aliphatic as well as aromatic α-aminocarboxylic acids can be split into their optical antipodes.

EXAMPLE 1

Preparation of a salt from 1-N-methyl ephedrine and N-salicylidine-d-p-hydroxyphenyl glycine in methanol A mixture of 16.7 g (0.10 mol) of DL-p-hydroxyphenyl glycine, 20.6 g (0.115 mol) of 1-N-methyl ephedrine, 14.0 g (0.115 mol) of salicyl aldehyde and 120 ml of methanol was stirred at 20° to 25° C. for about 64 hours. During the stirring procedure, the suspension turned intensely yellow at once. After about 1 hour, besides dissolution of the solid components, crystallization of a light yellow component was observed. To complete precipitation the reaction mixture was stirred for another hour in an ice bath. The crystal magma was filtered off and washed with 30 ml of a methanolether mixture (1:10). After drying at 50° C., 21.5 g of a salt of 1-N-methyl ephedrine and N-salicyliden-d-p-hydroxyphenyl glycine (95.4% of the theory, calculated on one enanthiomer) with a specific rotation $[\alpha]_D^{20}$ of +87.5° were obtained.

The following data were found for the salt of 1-N-methyl ephedrine and N-salicyliden-d-p-hydroxyphenyl glycine not yet known from the literature:

m.p.: 126°-126.5° C. (methanol) $[\alpha]_D^{20} = 91.6°$ (c=2, MeOH)

$^1$H-NMR (DMSO-d$_6$: δ(TMS) 0.95 (d,3; J=4.5 Hz); 2.64 (d,6); 3.18 (m,1); 5.08 (s,1); 5.22 (d,1; J=1.5 Hz); 6.7–7.5 (m,13); 8.56 (d,1); 8.0–9.5 (m,4).

elementary analysis for $C_{26}H_{30}N_2O_5$:
calculated: C 69.3, H 6.7, N 6.2
found: C 69.1, H 6.9, N 6.1.

In similar manner the following example was carried out using a solvent mixture of methanol/diethyl ether. 1-N-methyl-ephedrine and salicyl aldehyde were used in a 15% excess. The yield obtained is calculated on one enantiomer of the amino-acid. The range of errors of the specific rotations is about ±0.5%.

EXAMPLE 2

Amounts used: 0.025 mol
Solvents and volume thereof:
20 ml of methanol
20 ml of diethyl ether
Yield: 91.0%
$[\alpha]_D^{20}$ of crystallized salt: +84.2°

EXAMPLE 3

Preparation of a salt from 1-N-methyl ephedrine and N-salicyliden-d-valine in ethyl acetate A mixture of 11.7 g (0.10 mol) of DL-valine, 20.6 g (0.115 mol) of 1-N-methyl ephedrine, 14.0 g (0.115 mol) of salicyl aldehyde and 180 ml of methanol was stirred at room temperature for about 1 hour until dissolution was complete. Next, the solvent was removed under reduced pressure and the oily residue was taken up in 300 ml of ethyl acetate. The clear solution was seeded with a crystal of the salt of 1-N-methyl ephedrine and N-salicyliden-D-valine, whereupon a yellow, crystalline precipitate formed after a short stirring time at room temperature. The crystal magma was filtered off and washed with a small amount of ethyl acetate. After drying at 50° C., 5.65 g of the salt of 1-N-methyl ephedrine and N-salicyliden-D-valine were obtained; $[\alpha]_D^{20} = -49.2°$.

After concentration to half the volume and seeding of the solution, a further 8.60 g of the salt could be isolated having a specific rotation $[\alpha]_D^{20}$ of −48°.

The total yield of the salt of 1-N-methyl ephedrine and N-salicyliden-D-valine thus amounted to 71.2% of the theory. m.p. 129°–130° C. (ethyl acetate).

Elemental analysis for $C_{23}H_{32}N_2O_4$:
calculated: C 69.0%, H 8.1%, N 7.0%;
found: C 69.0%, H 8.2%, N 7.0%.

EXAMPLE 4

Preparation of a salt from 1-N-methyl ephedrine and N-salicyliden-D-phenyl alanine in ethyl acetate A mixture of 12.4 g (0.075 mol) of DL-phenyl alanine, 15.5 g (0.086 mol) of 1-N-methyl ephedrine, 10.5 g (0.086 mol) of salicyl aldehyde and 135 ml of methanol was stirred at room temperature for about 2 hours until dissolution was complete. The solvent was removed under reduced pressure and the oily residue taken up in 170 ml of ethyl acetate. The clear solution was seeded with a crystal of the salt of 1-N-methyl ephedrine and N-salicyliden-D-phenyl alanine, whereupon a yellow crystal magma formed after a short stirring at room temperature. The crystals were filtered off immediately and washed with a small amount of ethyl acetate. After drying at 50° C., 6.7 g (40% of the theory) of the salt of 1-N-methyl ephedrine and N-salicyliden-D-phenyl alanine having a specific rotation of $[\alpha]_D^{20}$ of +107.4° were obtained.

M.p. 119°–120.5° C. (ethyl acetate)
Elemental analysis for $C_{27}H_{32}N_2O_4$:
calculated: C 72.3%, H 7.2%, N 6.2%;
found: C 72.2%, H 7.2%, N 6.0%.

EXAMPLE 5

Preparation of a salt according to Example 1 with subsequent asymmetrical transformation of the second order in methanol 16.7 g of DL-hydroxyphenyl glycine (0.10 mol) and 20.6 g (0.115 mol) of l-N-methyl ephedrine were added to 125 ml of methanol, and the mixture was stirred for 44 hours at 16° to 17° C. and for about 1 hour in an ice bath. The mixture was then filtered and the separated crystals were washed with 15 ml of ether/methanol (10:1) and dried at 50° C. in a drying cabinet. The weakly yellow salt showed a specific rotation of $[\alpha]_D^{20} = +84.9°$; the yield was 20.2 g (89.7% of the theory, calculated on one enantiomer). The mother liquor was concentrated by evaporation under reduced pressure and then taken up in 40 ml of methanol. The mixture was left to stand for 18 hours at room temperature and then cooled to +6° C. for 6 hours. The precipitate was separated as described above, washed and dried. The weakly yellow salt showed a specific rotation $[\alpha]_D^{20} = +86.7°$; the yield was 3.0 g (13.3% of the theory, calculated on one enantiomer). The resulting mother liquor was again concentrated by evaporation under reduced pressure and taken up in 20 ml of methanol. The mixture was left to stand for 18 hours at room temperature and then cooled for 4 hours to +6° C. The precipitated weakly yellow salt was treated as described above, it had a specific rotation $[\alpha]_D^{20} = +87.14°$; the yield amounted to 5.1 g (22.6% of the theory, calculated on one enantiomer).

The mother liquor was again concentrated by evaporation under reduced pressure and taken up in 10 ml of methanol. After 72 hours at room temperature the mixture was cooled for 2 hours to +6° C. and the precipitated salt was washed with 40 ml of ether/methanol (10:1) and dried at 50° C. It had a specific rotation $[\alpha]_D^{20} = +90.1°$; the yield amounted to 5.2 g (23.1% of the theory, calculated on one enantiomer). Thus, a total yield of 33.5 g was obtained, corresponding to 148.7% of the theory, calculated on one enantiomer.

EXAMPLE 6

Preparation of a salt from d-threo-1-phenyl-2-dimethylaminopropane-1,3-diol and N-salicyliden-D-p-hydroxyphenyl glycine in methanol A mixture of 16.7 g (0.10 mol) of DL-p-hydroxyphenyl glycine, 22.4 g (0.115 mol) of d-threo-1-phenyl-2-dimethylaminopropane-1,3-diol, 14.0 g (0.115 mol) of salicyl aldehyde and 80 ml of methanol was stirred at room temperature. During stirring the suspension turned intensely yellow at once; dissolution was complete after about 1 hour. The clear solution was seeded with a crystal of the salt of d-threo-1-phenyl-2-dimethylaminopropane-1,3-diol and N-salicyliden-D-p-hydroxyphenyl glycine and, after addition of 80 ml of water, the solution was stirred for approximately 17 hours at room temperature to complete precipitation. The light yellow crystals were filtered off, washed with a small amount of methanol/ether (1:10) and dried at 50° C. 21.5 g of the salt of d-threo-1-phenyl-2-dimethylaminopropan-1,3-diol and N-salicyliden-D-p-hydroxyphenyl glycine (92.2% of the theory, calculated on one enantiomer) having a specific rotation of $[\alpha]_D^{20} = +115.9°$ were obtained.

EXAMPLE 7

Resolution of the salt of Example 1 and isolation of D(−)-p-hydroxyphenyl glycine To separate the salicyl aldehyde a solution of 20.2 g (0.045 mol) of the salt of l-N-methyl ephedrine and N-salicyliden-D-p-hydroxyphenyl glycine (Example 1) in 100 ml of hydrochloric acid (7.5% strength) was extracted three times, each time with 50 ml of methylene chloride. The remaining aqueous phase was concentrated in vacuo to about 40 ml and diluted with 20 ml of water. After heating to about 60° to 80° C., a pH of 6.8 was adjusted with about 16 ml of ammonia (25% strength) and the precipitated p-hydroxyphenyl glycine was separated by filtration. 5.39 g (71.9% of the theory) of D(−)-p-hydroxyphenyl glycine having a specific rotation of $[\alpha]_D^{20} = -154.6°$ (96.6% optical purity) were isolated. (c=1; 6 N HCl).

The aqueous mother liquor was adjusted to pH 12 with sodium hydroxide solution (10% strength); the light colored precipitate formed was filtered off with suction and washed with a small amount of aqueous ammonia (10% strength). 7.0 g (87.6% of the theory) of l-methyl ephedrine having a practically unchanged specific rotation were isolated.

For precipitation of the amino-acid the aqueous filtrate was concentrated to 50 ml, adjusted to pH 6.8 with 5 ml of concentrated hydrochloric acid and left to stand overnight for crystallization. A further 1.36 g of D-(−)-p-hydroxyphenyl glycine having a specific rotation of $[\alpha]_D^{20} = -135.5°$ and an optical purity of 84.7% were isolated. Hence, the total yield amounted to 90.0% of hydroxyphenyl glycine having an optical purity of 94%.

EXAMPLE 8

Resolution of the salt of Example 3 and isolation of D(−)-valine

For separation of salicyl aldehyde a solution of 13.5 g (0.034 mol) of the salt of l-N-methyl ephedrine and N-salicyliden-D-valine (Example 3) in 40 ml of hydrochloric acid (10% strength) was extracted three times, each time with 25 ml of methylene chloride. The remaining aqueous phase was adjusted to pH 12.5 with sodium hydroxide solution (35% strength) and the crystallizing methyl ephedrine separated by filtration. The solution was then adjusted to pH 6.8 with concentrated hydrochloric acid and the precipitated valine was filtered off. After drying, 2.1 g (53% of the theory) of D(−)-valine were obtained in the form of scaly, colorless crystals melting at 302° C., and having a specific rotation of $[\alpha]_D^{20} = -26°$; (c=1; 6 N HCl).

EXAMPLE 9

Resolution of the salt of Example 4 and isolation of D(+)-phenyl alanine

For separation of salicyl aldehyde a solution of 5.85 g (0.013 mol) of the salt of l-N-methyl ephedrine and N-salicylidin-D-phenyl alanine (Example 4) in 25 ml of hydrochloric acid (10% strength) was extracted three times, each time with 25 ml of methylene chloride. The remaining aqueous phase was adjusted to pH 12.5 with sodium hydroxide solution (35% strength) and the crystallizing N-methyl ephedrine was removed by filtration. The solution was then adjusted to pH 6.8 with concentrated hydrochloric acid and the precipitating phenyl alanine was filtered off. After drying, 1.3 g (60% of the theory) of D(+)-phenyl alanine were obtained in the form of colorless crystals; $[\alpha]_D^{20} = +16.7°$, (c=2; H₂O).

EXAMPLE 10

Resolution of the salt of Example 6 and isolation of D(−)-p-hydroxyphenyl glycine 10 ml of hydrochloric acid (37% strength) were added dropwise to a suspension of 22.5 g (0.0475 mol) of the salt of d-threo-1-phenyl-2-dimethylamino-propane-1,3-diol and N-salicyliden-D-p-hydroxyphenyl glycine (Example 6) in 130 ml of water until the precipitate had completely dissolved at pH 0.35. The precipitating salicyl aldehyde was separated and the aqueous phase was extracted with 75 ml of dichloroethane (3 times each time with 25 ml). The aqueous solution was then concentrated in a rotary evaporator to a volume of 50 ml and adjusted to pH 6.8 with about 7 ml of ammonia (25% strength) at 40° to 60° C. To complete precipitation the mixture was stirred for approximately 1 hour in an ice bath until it was cold. The crystal magma was filtered off with suction and dried at 50° C. 6.0 g (74.4% of the theory) of D(−)-hydroxyphenyl glycine were obtained in the form of colorless crystals having a specific rotation of $[\alpha]_D^{20} = 150.3°$ (93.9% optical purity); m.p. 227°–229° C. (c=1; 6N HCl).

What is claimed is:

1. A process for resolving a racemic DL-α-aminocarboxylic acid of the formula

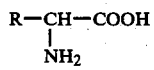

in which
R is isopropyl, phenyl, p-hydroxyphenyl or benzyl, which comprises
(a) in a medium selected from the group consisting of inert solvents and mixtures thereof, reacting said DL-α-aminocarboxylic acid with an aromatic aldehyde of the formula

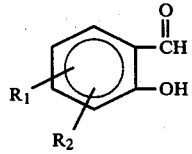

in which R₁ and R₂, which are identical or different, each is hydrogen or halogen, to form an azomethine derivative and in the same reaction stage reacting the azomethine derivative with an optically active tertiary amine having a dissociation constant of from $10^{-9}$ to $10^{-12}$ to form a mixture of diastereomeric salts;
(b) separating the mixture by crystallization into its component diastereomeric salts; and
(c) liberating an optically active α-aminocarboxylic acid by treating a separated salt with a strong acid.

2. A process as defined in claim 1, wherein the reaction of the aminocarboxylic acid with the aromatic aldehyde and the reaction of the azomethine derivative with the optically active tertiary amine are at a temperature in the range of from 0° C. to the boiling temperature of the reaction medium.

3. A process as defined in claim 1, wherein the reaction of the aminocarboxylic acid with the aromatic aldehyde and the reaction of the azomethine derivative with the optically active tertiary amine are performed with stirring for a period of from 1 to 160 hours at room temperature.

4. A process as defined in claim 1, wherein the reactants are thoroughly mixed by stirring for a period of from 1 to 160 hours until the reactants are completely dissolved and the product salt mixture has completely precipitated.

5. A process as defined in claim 1, wherein water set free in the reaction is not removed.

6. A process as defined in claim 1, wherein the medium is selected from the group consisting of lower aliphatic alcohols, admixtures of said alcohols and water, ethyl acetate, admixtures of ethyl acetate and water, dimethyl formamide and acetonitrile.

7. A process as defined in claim 1, wherein the optically active tertiary amine is selected from the group consisting of the D-isomers and L-isomers of N-methylephedrine or threo-1-phenyl-2-dimethylamino-propane-1,3-diol.

8. The process as defined in claim 1, wherein the aromatic aldehyde is an o-hydroxybenzaldehyde.

9. A process as defined in claim 1, wherein equimolar amounts of the aminocarboxylic acid and aromatic aldehyde and the optically active tertiary amine are reacted.

10. The process as defined in claim 1, wherein a diastereomeric compound of the formula

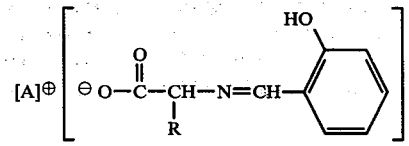

in which A is a cation formed by addition of a proton to the nitrogen atom of an optically active tertiary amine base and R is p-hydroxyphenyl, benzyl or isopropyl, is formed as the salt of the optically active amine base and the azomethine derivative.

11. A process as defined in claim 1, wherein said reactants are mixed with one another.

12. A process for resolving a racemic DL-α-aminocarboxylic acid of the formula

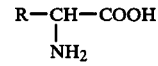

in which
R is isopropyl, phenyl, p-hydroxyphenyl or benzyl, which comprises
(a) in a medium selected from the group consisting of inert solvents and mixtures thereof and at a temperature in the range of from 0° C. to the boiling temperature of said medium and while stirring for a period of from 1 to 160 hours, reacting said DL-α-aminocarboxylic acid with an aromatic aldehyde of the formula

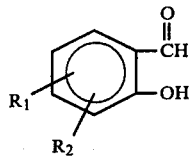

in which $R_1$ and $R_2$, which are identical or different, each is hydrogen or halogen, to form an azomethine derivative and in the same reaction stage reacting the azomethine derivative with an optically active tertiary amine having a dissociation constant of from $10^{-9}$ to $10^{-12}$ to form a mixture of diastereomeric salts;

(b) separating the mixture by crystallization into its component diastereomeric salts;

(c) liberating an optically active α-aminocarboxylic acid by treating a separated salt with a strong acid.

13. A process for resolving a racemic DL-α-aminocarboxylic acid of the formula

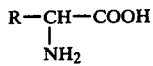

in which
R is isopropyl, phenyl, p-hydroxylphenyl or benzyl, which comprises
(a) in a medium selected from the group consisting of inert solvents and mixtures thereof and at a temperature in the range of from 0° C. to the boiling temperature of the reaction medium and without removal of the water set free during reaction, reacting DL-α-aminocarboxylic acid with an aromatic aldehyde of the formula

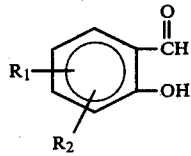

in which $R_1$ and $R_2$, which are identical or different, each is hydrogen or halogen, to form an azomethine derivative and in the same reaction stage reacting the azomethine derivative with an optically active tertiary amine having a dissociation constant of from $10^{-9}$ to $10^{-12}$ to form a mixture of diastereomeric salts;

(b) separating the mixture by crystallization into its component diastereomeric salts;

(c) liberating an optically active α-aminocarboxylic acid by treating a separated salt with a strong acid.

14. The process as defined in claim 13, wherein the reaction is carried out at room temperature.

15. A compound of the formula

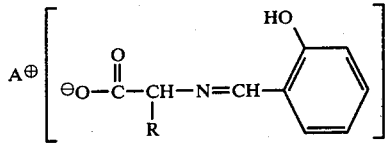

in which $A^{\oplus}$ is a cation formed by addition of a proton to the nitrogen atom of an optically active tertiary amine having a dissociation constant of from $10^{-9}$ to $10^{-12}$, and in which R is isopropyl, p-hydroxyphenyl or benzyl.

16. A compound which is the salt of d-N-methyl ephedrine and N-salicyliden-p-hydroxyphenyl glycine.

17. A compound which is the salt of l-N-methyl ephedrine and N-salicyliden-p-hydroxyphenyl glycine.

18. A compound which is the salt of d-N-methyl ephedrine and N-salicyliden-phenyl glycine.

19. A compound which is the salt of l-N-methyl ephedrine and N-salicyliden-phenyl alanine.

20. A compound which is the salt of d-N-methyl ephedrine and N-salicyliden-valine.

21. A compound which is the salt of l-N-methyl ephedrine and N-salicyliden-valine.

22. A compound which is the salt of d-1-phenyl-2-dimethylaminopropane-1,3-diol and N-salicyliden-hydroxyphenyl glycine.

23. A compound which is the salt of l-1-phenyl-2-dimethylaminopropane-1,3-diol and N-salicyliden-p-hydroxyphenyl glycine.

* * * * *